United States Patent [19] [11] 4,424,397
Hoene et al. [45] Jan. 3, 1984

[54] FORMALDEHYDE PROCESS

[75] Inventors: David J. Hoene; John L. Riggs, both of Wilmington, Del.

[73] Assignee: E. I. Du Pont de Nemours and Company, Wilmington, Del.

[21] Appl. No.: 425,049

[22] Filed: Sep. 27, 1982

[51] Int. Cl.³ .......................................... C07C 47/052
[52] U.S. Cl. .................................... 568/473; 568/472
[58] Field of Search ................................ 568/473, 472

[56] References Cited
U.S. PATENT DOCUMENTS

| | | | |
|---|---|---|---|
| 4,010,208 | 3/1977 | Aicher et al. | 568/473 |
| 4,076,754 | 2/1978 | Kiser et al. | 568/473 |
| 4,167,527 | 9/1979 | Nielson | 568/473 |
| 4,208,353 | 6/1980 | Webster et al. | 568/473 |
| 4,219,509 | 8/1980 | Nielson et al. | 568/473 |
| 4,306,089 | 12/1981 | Webster et al. | 568/473 |

Primary Examiner—Werren B. Lone

[57] ABSTRACT

A process for the oxidative dehydrogenation of methanol to form formaldehyde using silver crystals as catalyst which silver crystals are supported on a screen formed of an alloy containing at least 20 weight percent gold and the remainder silver is disclosed.

5 Claims, 1 Drawing Figure

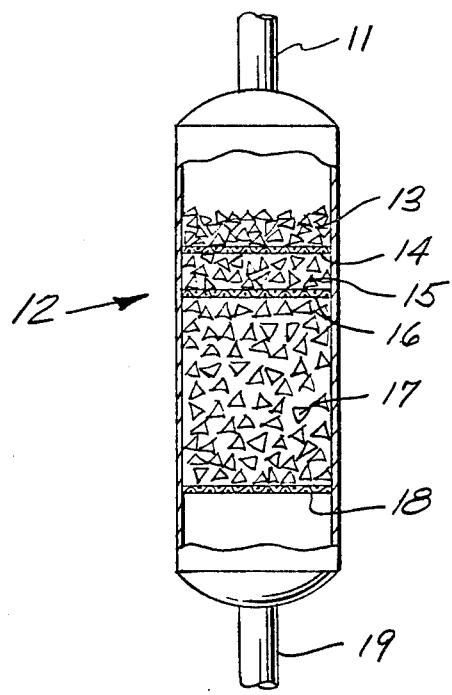

FORMALDEHYDE PROCESS

FIELD OF THE INVENTION

The present invention relates to the production of formaldehyde from methanol using layers of silver crystals, each supported on a screen, as the catalyst.

PRIOR ART

U.S. Pat. No. 4,010,208 discloses converting methanol to formaldehyde using a bed of silver crystals comprising a plurality of layers wherein the particle size of the catalyst varies from layer to layer.

SUMMARY OF THE INVENTION

In carrying out the process of the present invention, the methanol feedstock is first vaporized then mixed with an oxygen containing gas and fed to the reactor containing silver catalyst. The reaction mechanism is believed to be a combination of dehydrogenation and oxidation of methanol.

$$CH_3OH \rightarrow HCHO + H_2$$

$$CH_3OH + \tfrac{1}{2}O_2 \rightarrow HCHO + H_2O$$

Silver-catalyzed processes for making formaldehyde from methanol can be characterized according to the number of catalytic stages used to effect the conversion. Single stage operation is widely used, but suffers from the disadvantage that rather high amounts of unconverted methanol are contained in the product emerging from the catalyst bed. To eliminate this problem of methanol leakage, two silver catalytic stages can be used in conjunction with interstage cooling. Alternatively the second stage can use a metal oxide catalyst such as described in U.S. Pat. No. 2,519,788.

BRIEF DESCRIPTION OF THE DRAWING

The drawing is a schematic view of the reactor used in carrying out the present invention.

DETAILED DESCRIPTION OF THE DRAWING

A mixture of methanol, air and optionally water is fed to inlet 11 of the reactor referred to generally at 12, the mixture passes through a first layer of silver crystals 13, supported on a screen 14, a second layer of silver crystals 15, supported on screen 16 and finally a third layer of silver crystals 17 supported on screen 18 the product formaldehyde is then removed through outlet 19 and absorbed by water in the conventional manner.

DETAILED DESCRIPTION

In the vapor phase oxidative dehydrogenation of methanol with air to provide formaldehyde, activity of the silver catalyst is a function of the surface area and therefore particle size of the silver crystals. Pressure drop through the catalyst is an inverse function of the particle size of the silver crystals. To optimize performance, catalyst beds are sometimes constructed using layers of silver catalyst crystals with each layer containing a different size range of silver crystals.

When small silver crystals are poured onto a layer of larger crystals, the small crystals sift down into the voids between the larger crystals which markedly increases pressure drop through bed over what it would have been if the layers had remained separated.

Small mesh screens can be placed between the layers of crystals to prevent the phenomenon described above. However, at the reaction conditions of 600+° C. in the presence of oxygen, most known metals become catalytic and promote carbon and carbon oxides formation and thus reduce the selectivity of the silver catalyst bed.

Small mesh silver screens (gauze) can be used to separate layers of different sized silver crystals and reduce pressure drop without affecting bed selectivity. However, at reaction conditions both silver gauze and crystals undergo extensive dendritic growth which reduces voidage at the gauge-control interface, restricts flow and increases pressure drop.

It has now been found that a small mesh screen or gauze made from a gold/silver alloy can be used, without affecting bed selectivity, to separate layers of different sized silver crystals and markedly reduce pressure drop below that for a similar bed separated by silver gauze. Gold is essentially inert at reaction conditions and therefore does not affect bed selectivity. It also raises the melting point of the gauze which therefore does not undergo dentritic growth to restrict flow at the gauze-control interface.

Ultimate production capacities of formaldehyde plants are usually limited by pressure drop through the catalyst beds. Since the gold and silver content of the subject gauze can be recovered and reused, this invention provides a relatively inexpensive method to increase capacities of plants using multilayered catalyst beds.

The screen should be formed of at least 20 wt % gold and the remainder silver. While a 100% gold screen can be used, a gold-silver alloy provides satisfactory performance and is less expensive. While screens are used in the appended Examples it is to be understood that any foraminous member of the appropriate porosity, such as a sheet with holes in it, can be used.

Generally the methanol feedstock is vaporized, superheated, mixed with air and any recycled gases and then fed to the silver catalyzed reactor which is operated at from 550° to 750° C. Optionally the product gases from the reactor can be mixed with additional air and sent to a second reactor, which can either be silver or metal oxide catalyst, to increase conversion of methanol or formaldehyde. The gases finally are sent to an absorber where they are cooled to 25° to 45° C. Product formaldehyde in water, 40 to 60% formaldehyde, is removed from the absorber.

EXAMPLES

Example 1

A semi-works scale reactor 0.8 inch (0.02 m) inside diameter is fitted with a multilayered bed of silver crystals as shown in the drawing. The supporting and separating screens for each layer (14), (16) and (18) are 100 mesh (U.S. sieve series) formed of 75 wt % gold and 25 wt % silver. The bottom screen (18) is supported by quartz wool.

Fifty grams of silver crystals (17) which pass an 8 mesh (U.S. sieve series) screen and are retained on an 18 mesh (U.S. sieve series) screen are placed on the bottom screen (18). A second screen (16) is inserted on top of the catalyst just installed and on top of it are placed 10 grams of silver crystals (15) which pass a 20 mesh (U.S. sieve series) screen and are retained on a 40 mesh (U.S. sieve series) screen. A third screen (14) is inserted on top of the catalyst just installed and on top of it are placed 10 grams of silver crystals (13) which pass a 40 mesh (U.S. sieve series) screen and are retained on a 60 mesh (U.S. sieve series) screen. A mixture of 26 mol % methanol, 23 mol % water and 51% air is heated to 120° C. and fed to the reactor at a rate of about 50 grams per minute. The gases exiting the reactor are at 686° C. The methanol conversion is 94.0% and the methanol to formaldehyde selectivity is 90.2%. After one month of operation the pressure drop across the reactor is 2.3 psig ($16 \times 10^3$ Pa).

EXAMPLE 2 (CONTROL)

A semi-works scale reactor 0.8 inch (0.02 m) inside diameter is fitted with a multilayered bed of silver crystals as shown in the drawing. The supporting and separating screens for each layer (14), (16) and (18) are 20 mesh (U.S. sieve series) silver screens. The bottom screen (18) is supported by quartz wool.

Twenty-five grams of silver crystals (17) which pass an 8 mesh (U.S. sieve series) screen and are retained on a 16 mesh (U.S. sieve series) screen are placed on the bottom screen (18). A second screen (16) is inserted on top of the catalyst just installed and on top of it are placed 10 grams of silver crystals (15) which pass a 20 mesh (U.S. sieve series) screen and are retained on a 40 mesh (U.S. sieve series) screen. A third screen (14) is inserted on top of the catalyst just installed and on top of it are placed 10 grams of silver crystals (13) which pass a 40 mesh (U.S. sieve series) screen and are retained on a 60 mesh (U.S. sieve series) screen. A mixture of 24 mol % methanol, 25 mol % water, 4 mol % formaldehyde and 47 volume % air is heated to 120° C. and fed to the reactor at a rate of about 50 grams per minute. The gases exiting the reactor are at 704° C. The methanol conversion is 94.2% and the methanol to formaldehyde selectivity is 89.9%. After one month the pressure drop across the reactor is 7.4 psig ($51 \times 10^3$ Pa).

We claim:

1. In a process of oxidative dehydrogenation of methanol to produce formaldehyde comprising contacting methanol with oxygen at from about 550° to about 750° C. using layers of different size silver crystals as catalyst, the improvement wherein at least one of the layers of silver crystals is separated from the others and supported by a foraminous member formed of 20 to 100 percent by weight gold and the remainder consisting essentially of silver.

2. The process of claim 1 wherein the foraminous member is a screen.

3. The process of claim 2 wherein the screen is made from an alloy containing about 75 weight percent gold and 25 weight percent silver.

4. The process of claim 1 wherein all of the silver crystals are separated and supported on foraminous members.

5. The process of claim 4 wherein the foraminous members are screens made of an alloy of about 75 percent by weight gold and about 25 weight percent silver.

* * * * *

UNITED STATES PATENT OFFICE
CERTIFICATE OF CORRECTION

PATENT NO. : 4,424,397
DATED : January 3, 1984
INVENTOR(S) : David J. Hoene and John L. Riggs It is certified that error appears in the above-identified patent and that said Letters Patent are hereby corrected as shown below:

In column 2, line 12, "gauge-control" is corrected to read --gauze-crystal--.

In column 2, line 23, "gauze-control" is corrected to read --gauze-crystal--.

Signed and Sealed this

Twenty-fourth Day of April 1984

[SEAL]

*Attest:*

*Attesting Officer*

GERALD J. MOSSINGHOFF

*Commissioner of Patents and Trademarks*